(12) United States Patent
Sandstrom et al.

(10) Patent No.: US 7,637,916 B2
(45) Date of Patent: Dec. 29, 2009

(54) MEDICAL ELECTRICAL LEAD IMPLANT TOOL

(75) Inventors: Richard D. Sandstrom, Scandia, MN (US); Keith A. Ufford, Chisago City, MN (US); James R. Svensk, Coon Rapids, MN (US)

(73) Assignee: Medtronic, Inc., Minneapols, MN (US)

( * ) Notice: Subject to any disclaimer, the term of this patent is extended or adjusted under 35 U.S.C. 154(b) by 929 days.

(21) Appl. No.: 10/858,228

(22) Filed: Jun. 1, 2004

(65) Prior Publication Data

US 2005/0267554 A1  Dec. 1, 2005

(51) Int. Cl.
*A61B 19/00* (2006.01)

(52) U.S. Cl. .......................................... 606/129; 607/1

(58) Field of Classification Search .................. 606/129; 600/377, 386, 434; 607/116, 117, 126, 127
See application file for complete search history.

(56) References Cited

U.S. PATENT DOCUMENTS

| 4,207,903 | A | | 6/1980 | O'Neill |
| 5,036,854 | A | | 8/1991 | Schollmeyer et al. |
| 5,290,299 | A | | 3/1994 | Fain et al. |
| 5,354,326 | A | * | 10/1994 | Comben et al. ............. 607/115 |
| 5,752,915 | A | * | 5/1998 | Neubauer et al. ........... 600/373 |
| 5,902,289 | A | * | 5/1999 | Swartz et al. ............... 604/530 |
| 6,010,526 | A | * | 1/2000 | Sandstrom et al. ............. 607/1 |
| 2003/0120264 | A1 | | 6/2003 | Lattouf |

FOREIGN PATENT DOCUMENTS

| WO | 03090833 A1 | 11/2003 |
| WO | WO2004041349 A | 5/2004 |

* cited by examiner

*Primary Examiner*—Michael J Milano
*Assistant Examiner*—Victor X Nguyen
(74) *Attorney, Agent, or Firm*—Carol F. Barry

(57) ABSTRACT

A medical electrical lead implant tool includes a gripping assembly, terminating a distal end of an elongate shaft, adapted to alternately grasp the lead and release the lead and to rotate the lead, and a user control terminating a proximal end of the shaft. An internal drive cable extends within the shaft coupling the gripping assembly to the user control. The user control facilitates single-handed manipulation of a slidable dial, which may be grasped by fingers of a hand for longitudinal and rotational manipulation when a stationary handle is held in a palm of the hand; the longitudinal manipulation causing the gripping assembly, via the drive cable, to alternately grasp the lead and release the lead and the rotational manipulation causing the gripping assembly, via the drive cable, to rotate the lead.

12 Claims, 5 Drawing Sheets

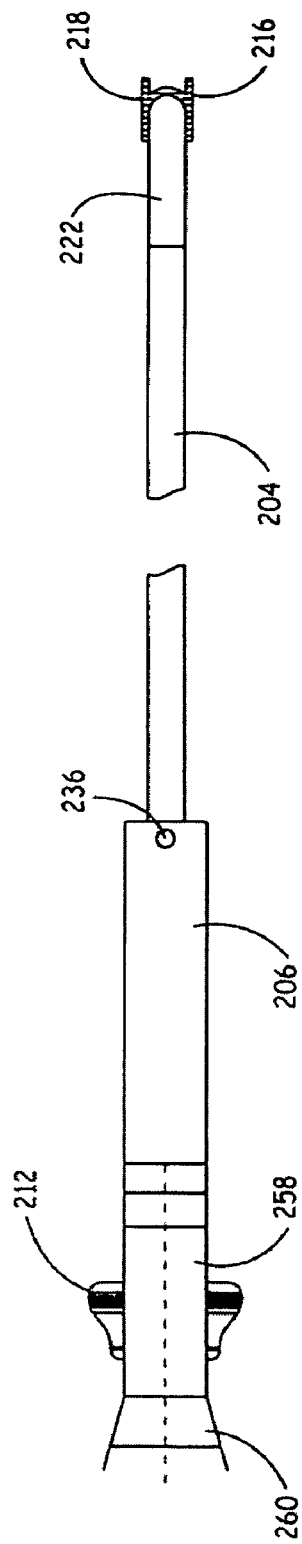
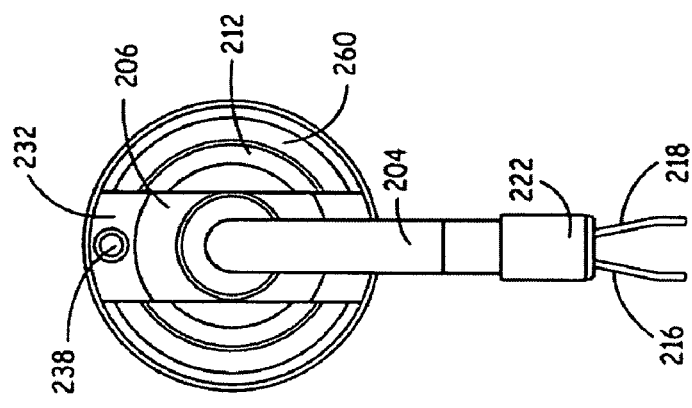
FIG. 2
FIG. 3

MEDICAL ELECTRICAL LEAD IMPLANT TOOL

FIELD OF THE INVENTION

The present invention relates generally to a medical electrical lead implant tool, and more particularly to a tool facilitating the implantation leads having at least one fixation helix or the like in areas not readily accessible during surgery.

BACKGROUND OF THE INVENTION

It is well known in the medial field that electrode leads capable of delivering electrical shocks may be implanted in a patient's body to stimulate a particular area or organ therein. Such leads may be positioned, for example, proximate a patient's heart to treat very fast, and potentially lethal, cardiac arrhythmias. Typically, such epicardial leads are coupled to an implantable cardiac device (ICD) which continuously monitors the heart's electrical signals and senses if, for example, the heart is beating dangerously fast. If this condition is detected, the ICD can deliver one or more electric shocks within a few seconds to return the heart to a normal heart rhythm.

Electrode leads of the type described above may be secured within a patient's body by at least one fixation helix. This fixation device often serves as an electrode and is inserted (i.e. screwed) into an area of human tissue such as an epicardial surface. Implant tools capable of guiding an electrode lead to and rotating the attached fixation helix into an implant site are known and typically comprise a distal gripping assembly for engaging (i.e. loading) part of a lead (e.g. the head) coupled to a proximal handle. During implantation, a surgeon engages a lead with the tool, positions it at the implant site, implants the lead (i.e. screws the lead's fixation helix into an area of tissue), and lastly disengages the lead from the tool. In some cases implantation may be accomplished by rotating the entire tool, but, in many cases, wherein the site of implantation is not readily accessible (e.g. a posterior epicardial surface accessed via a thoracotomy), this is not practical. Thus, to facilitate the implant of electrical leads in difficult-to-reach areas, implant tools, which permit remote rotation of the gripping assembly, have been developed. It is desirable to provide a lead implant tool that may be effectively utilized with one hand for the engagement, positioning, implant (e.g. via remote rotation of the gripping assembly), and disengagement of an electrical lead.

BRIEF DESCRIPTION OF THE DRAWINGS

The present invention will hereinafter be described in conjunction with the following figures, wherein like reference numerals denote like elements, and FIGS. 1, 2, and 3 are side, top, and end plan views, respectively, of an electrode lead implant tool in accordance with the present invention;

DETAILED DESCRIPTION OF THE INVENTION

The following detailed description of the invention is merely exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
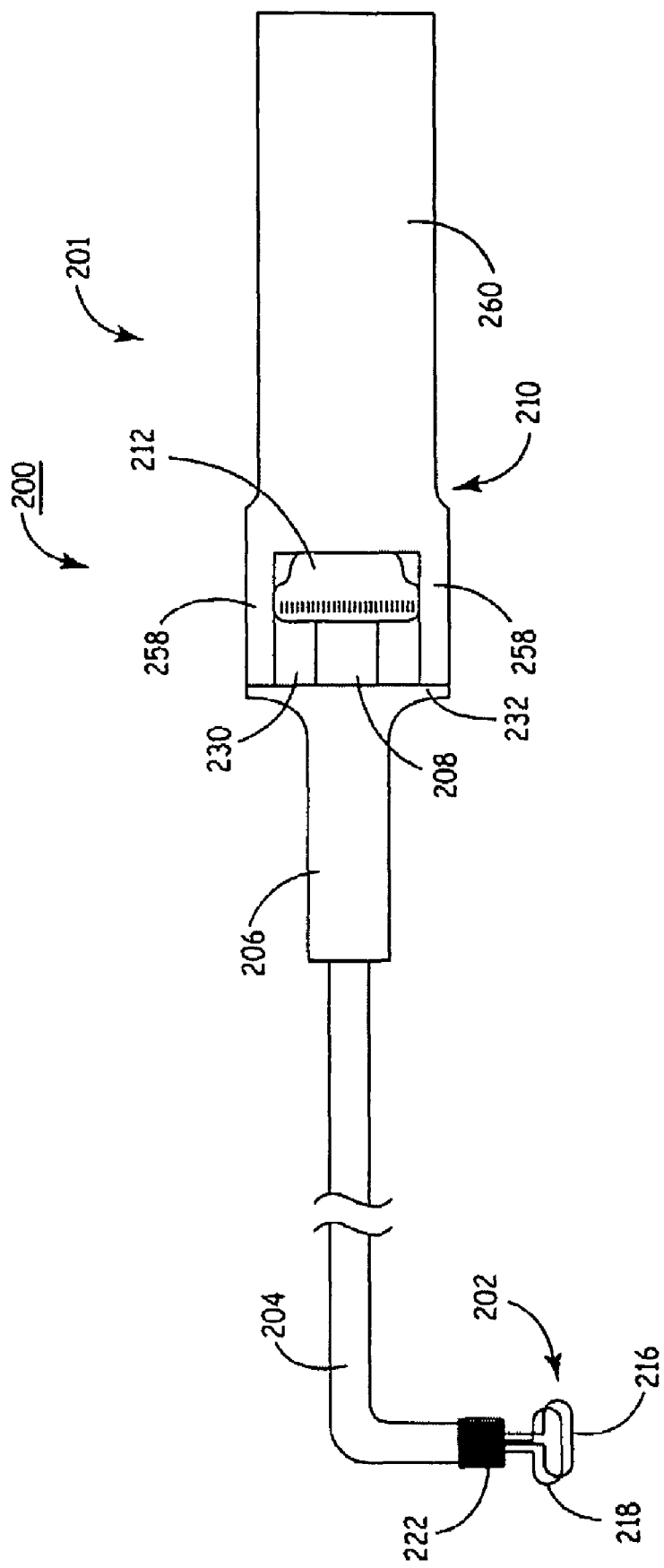

FIG. 1 is a side plan view of a medical electrical lead implant tool 200 according to one embodiment of the present invention. FIG. 1 illustrates tool 200 including a gripping assembly 202, formed by a nose piece 222 and tongs 216 and 218, and medial shaft portion 204, extending proximally from nose piece 222, each of which are similar to those described in commonly assigned U.S. Pat. No. 6,010,526 which is incorporated by reference in its entirety herein. FIG. 1 further illustrates tool 200 including a user control 201 terminating a proximal end of medial shaft portion 204; the user control 201 is configured for single-handed operation and includes a slidable dial 212, a shaft guide member 206, and a stationary handle 210. The proximal end of shaft 204 is received by an opening at a distal end of shaft guide member 206; a proximal end 232 of shaft guide member 206 expands to form a bell-shaped mouth that receives a distal end of handle 210. Specifically, proximal end 232 abuts two fingers (i.e. extensions) 258 which are distinct from a body 260 of handle 210 and extend distally from handle body 260. The outer edges of the upper and lower interfaces formed by fingers 258 and proximal end 232 are thus substantially smooth as can be seen in FIGS. 2 and 3, which are top and end plan views of implant tool 200.

Referring still to FIG. 1, it can be seen that slidable dial 212 is positioned between fingers 258 and around a retainer rod 208, whose distal and proximal ends are held within the proximal end of shaft guide member 206 and the distal end of handle 210, respectively. Retainer rod 208 is fixedly coupled to slidable dial 212 and may rotate and/or move longitudinally between shaft guide member 206 and handle 210 as is more fully described hereinbelow. Access to slidable dial 212 is facilitated via windows 230 which are provided on either side of fingers 258 so that implant tool 200 is configured to enable an operator to simultaneously grasp proximal handle portion 210 with one hand (e.g. with the palm) and move (i.e. rotate and/or move longitudinally) slidable dial 212 with the same hand (e.g. with the thumb). Slidable dial 212 is shown in FIG. 3 as having a first, distal section of a larger diameter, which tapers inward to a second, proximal section of a smaller diameter. Slidable dial 212 is thus contoured and provided with a plurality of grooves therein to facilitate user control (i.e. to provide a better, more ergonomic grip, etc.). It should be understood, however, that slidable dial 212 may take any shape suitable for permitting longitudinal and rotational manipulation thereof.

Two fastening devices that cannot be seen in FIG. 1 may be seen in FIGS. 2 and 3. FIG. 2 illustrates a fastening device 236 (e.g. a set screw) positioned within the distal portion of shaft guide member 206 to secure medial shaft 204 within shaft guide member 206. FIG. 3 illustrates another fastening device 238 (e.g. a screw) positioned in an upper front of the proximal end of shaft guide member 206 to couple shaft guide member 206 to fingers 258 of handle 210. A third fastening device 240 (e.g. a screw), which is positioned within lower front of the proximal end of shaft guide member 206, also couples shaft guide member 206 to handle 210 and may be seen in FIG. 4.

Although fastening devices 236, 238, and 240 are shown as having particular locations along shaft guide member 206, it should be appreciated that they may assume any suitable position within implant tool 200 and may be accompanied by additional fastening devices.

Figure 4:
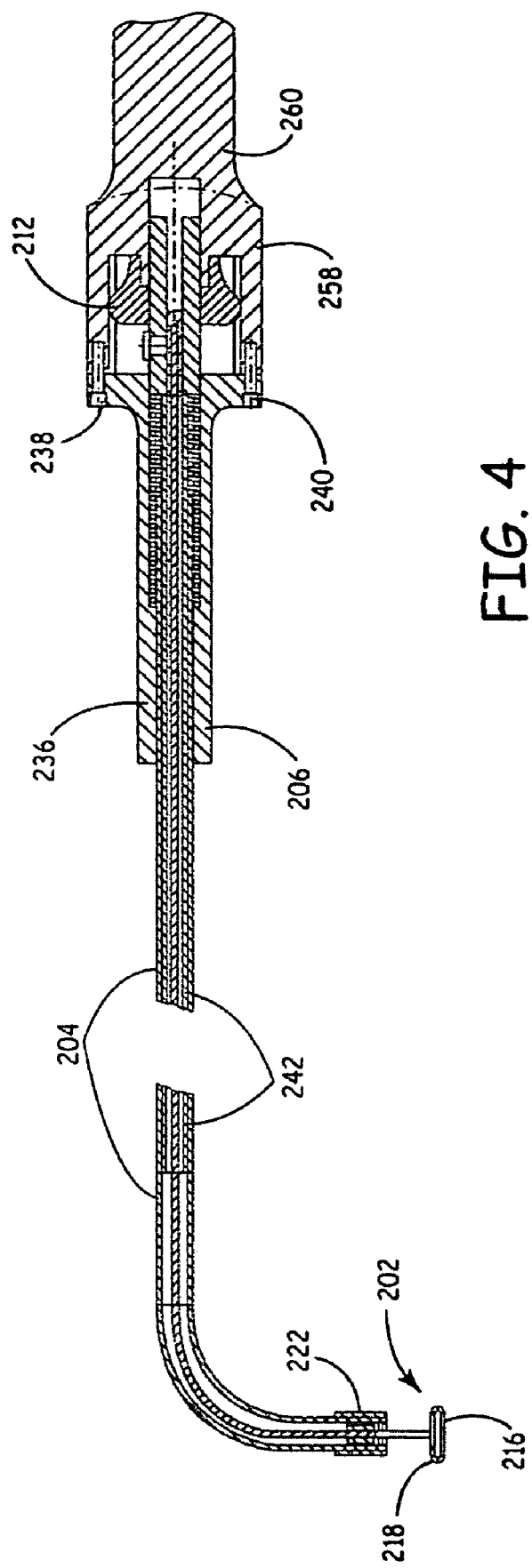
FIG. 4 is a general side cross-sectional view of the electrode lead implant tool shown in FIGS. 1-3.

FIG. 4 is a side cross-sectional view of the electrode lead implant tool 200 shown in FIGS. 1-3. FIG. 4 illustrates the distal end and the proximal end of shaft 204 extending substantially into nose piece 222 and shaft guide member 206, respectively, and an internal drive cable 242 passing through shaft 204, nose piece 222, and shaft guide member 206 in order to couple gripping assembly 202 to slidable dial 212. Cable 242 permits the transfer of forces (e.g. torque) from slidable dial 212 to gripping assembly 202.

Figure 5:
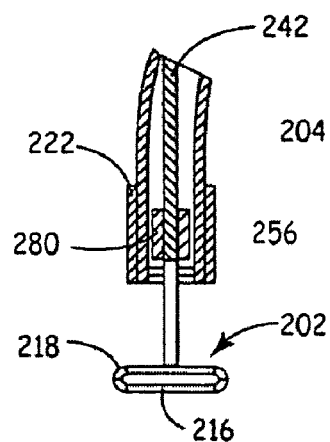
FIG. 5 is a detailed side cross-sectional view of the shaft, nose piece, and gripping assembly of the electrode lead implant tool shown in FIGS. 1-4.

FIG. 5 is a detailed side cross-sectional view of gripping assembly 202 and shaft 204 of the electrode lead implant tool 200 shown in FIGS. 1-4. FIG. 5 illustrates a distal end of cable 242 terminating within nose piece 222 where cable 242 is coupled (e.g. crimped) to proximal ends of tongs 216 and 218 by means of a crimp sleeve 280. FIG. 5 further illustrates a toroidal bearing 256 positioned within the distal end of nose piece 222 and extending around tongs 216 and 218; tongs 216 and 218 slide along toroidal bearing 256 and are forced closer together during cable retraction and permitted to move apart during cable extension in response to slidable dial 212 moving away from and closer to shaft guide member 206, respectively. It should thus be understood that longitudinal movement of slidable dial 212 in a first direction (i.e. away from shaft guide member 206) causes the distal ends of tongs 216 and 218 to move toward nose piece 222 and therefore closer to one another. Longitudinal movement of slidable dial 212 in the opposite direction (i.e. toward shaft guide member 206) causes the distal ends of tongs 216 and 218 to extend from nose piece 222 and move away from each other. In this manner, slidable dial 212 may be manipulated to cause tongs 216 and 218 to engage (i.e. grip) and disengage (i.e. release) a lead.

Figure 6:
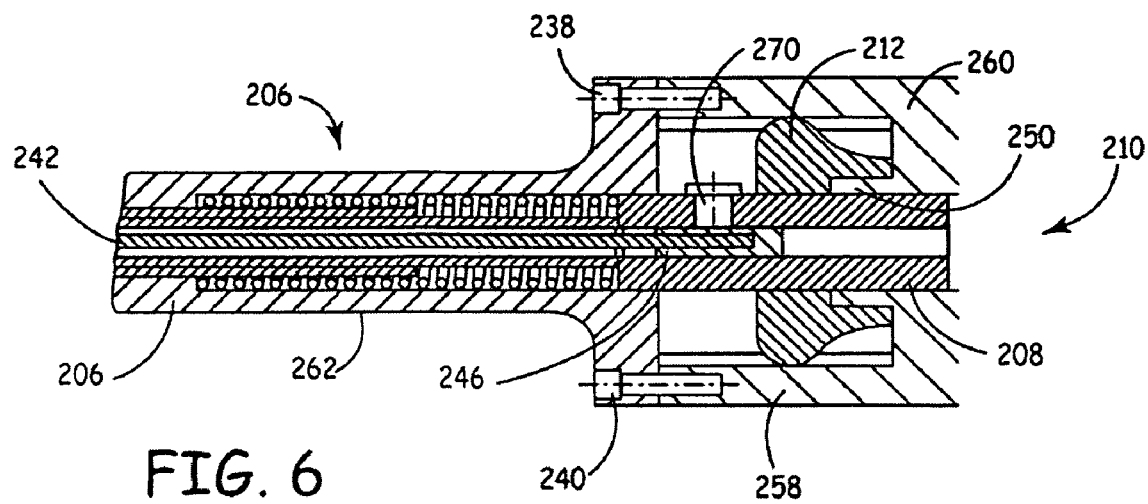
FIG. 6 is a detailed side cross-sectional view of a portion of the handle and shaft guide member of the electrode lead implant tool shown in FIGS. 1-5.

FIG. 6 is a detailed side cross-sectional view of handle 210 and shaft guide member 206 of the electrode lead implant tool 200 shown in FIGS. 1-5. FIG. 6 illustrates a proximal end of cable 242 extending into shaft guide member 206 and received therein by a sleeve 246; cable 242 is secured therein by a compression means 270 (e.g. a set screw) that compresses sleeve 246 so that an inner surface thereof frictionally engages an outer surface of cable 242. It can be seen in FIG. 6 that sleeve 246 is secured within retainer rod 208, which is, in turn, fixedly coupled to slidable dial 212. Thus, force applied to slidable dial 212 is transferred through retainer rod 208, sleeve 246, and cable 242 to tongs 216 and 218.

FIG. 6 further illustrates handle 210 including an annular extension 250, which extends distally near the distal end of handle body 260, around the proximal end of retainer rod 208 and is partly received by a cavity provided within a proximal end of slidable dial 212. Slidable dial 212 may rotate and/or move longitudinally relative to annular extension 250; however, slidable dial 212 is prevented from extending so far as to disengage from annular extension 250 (e.g. by the proximal end of shaft guide member 206). Annular extension 250 thus helps maintain the positioning of retainer rod 208 and slidable dial 212 without interfering with the rotational and/or longitudinal movement thereof.

As can be further seen in FIG. 6, an internal cable tension spring 262 is provided within shaft guide member 206, a proximal end of which abuts retainer rod 208 while a distal end thereof abuts an inner step or wall of shaft guide member 206. According to the illustrated embodiment, retainer rod 208 moves along with slidable dial 212 such that a distal movement of slidable dial 212 (i.e. towards shaft guide member 206) results in the compression of cable tension spring 262; once a force sufficient to move slidable dial 212 towards shaft guide member 206 is removed, spring 262 will expand proximally to force slidable dial 212 away from shaft guide member 206. As has been described hereinabove, movement of slidable dial 212 away from shaft guide member 206 results in the corresponding movement of tongs 216 and 218 in the direction of nose piece 222 and toward each other. A user of implant tool 200 may thus push slidable dial 212 towards shaft guide member 206 to open tongs 216 and 218, and then release slidable dial 212 (i.e. cease applying a longitudinal force thereto) to allow tongs 216 and 218 to close around a lead. If a lead is engaged as tongs 216 and 218 close, the implant will be secured therebetween by the tension generated by spring 262. In this way, tongs 216 and 218 may maintain a grip on an implant until an operator chooses to release the implant by once again sliding slidable dial 212 towards shaft guide member 206.

Figure 7:
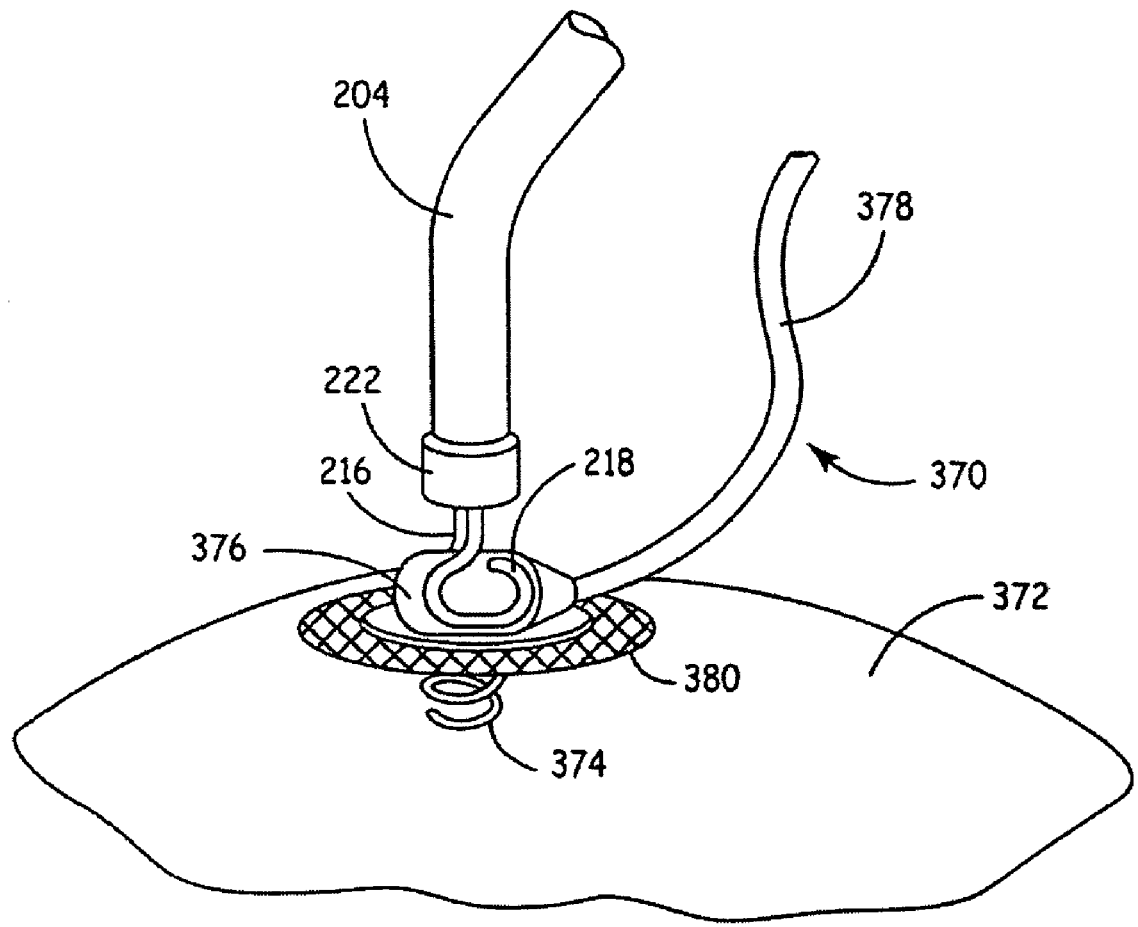
FIG. 7 is schematic of the electrode lead implant tool shown in FIGS. 1-6 positioning a lead electrode for implantation.

It should thus be understood that tool 200 may utilized to engage or grip, position, implant, and disengage from or release a lead having a fixation helix affixed thereto in the manner suggested in FIG. 7. FIG. 7 illustrates a medical electrical lead 370 including a fixation helix 374 extending from a head 376 which is coupled to a lead body 378; head 376 is engaged by tongs 216 and 218 of implant tool 200 and positioned via shaft 204 of tool 200 for implantation in an epicardial surface 372. Insulative lead body 378 contains an elongated conductor that is coupled to fixation helix 374, which serves as an electrode. Fixation helix 374 extends downward from a lower surface of lead head 376, which carries around its external periphery a mesh skirt 380 (e.g. made of a DACRON fiber).

According to embodiments of the present invention, engagement of lead head 376 is accomplished by first pushing slidable dial 212 toward shaft guide member 206, resulting in the compression of cable tension spring 262 and the opening of tongs 216 and 218. The distal ends of tongs 216 and 218 are then placed proximate lead head 376 and allowed to close (i.e. the longitudinal force applied to slidable dial 212 is removed). Engagement is maintained as cable tension spring 262 attempts to expand thereby placing a constant gripping tension on the distal ends of tongs 216 and 218. After lead engagement, shaft 204 is maneuvered to position tongs 216 and 218 in proximity to epicardial surface 372 so as to position fixation helix 374 at an implant site. After helix 374 is implanted in epicardial surface 372, via rotation of slidable dial 212, lead head 376 is released by once again by longitudinally moving slidable dial 212 toward shaft guide member 206 and causing the distal ends of tongs 216 and 218 to separate.

Finally, it will be appreciated by those skilled in the art that while the invention has been described above in connection with a particular embodiment, the invention is not necessarily so limited; numerous other embodiments and uses are intended to be encompassed by the claims attached hereto.

What is claimed is:

1. A medical electrical lead implant tool, comprising:
    an elongate shaft including a proximal end and a distal end;
    a gripping assembly terminating the distal end of the shaft and adapted to alternately grasp the lead and release the lead and to rotate the lead;
    a drive cable coupled to the gripping assembly and extending proximally therefrom within the shaft; and
    a user control terminating the proximal end of the shaft and including a shaft guide member coupled to the shaft, a stationary handle coupled to the shaft guide member, a slidable and rotatable dial coupled to a proximal end of the drive cable and positioned in between the shaft guide member and the stationary handle, and an aperture formed between the shaft guide member and the handle to expose the slidable and rotatable dial;

wherein the user control facilitates single-handed manipulation of the slidable, rotatable dial, which may be grasped by fingers of a hand for longitudinal and rotational manipulation when the stationary handle is held in a palm of the hand; the longitudinal manipulation causing the gripping assembly, via the drive cable, to alternately grasp the lead and release the lead and the rotational manipulation causing the gripping assembly, via the drive cable, to rotate the lead.

2. The tool of claim 1, wherein said shaft is curved.

3. The tool of claim 1, wherein the gripping assembly comprises a pair of tongs and wherein the longitudinal manipulation of the slidable, rotatable dial in a first direction causes the tongs to spread apart to release the lead.

4. The tool of claim 3, wherein said first direction is a distal direction.

5. The tool of claim 3, wherein the first direction is a proximal direction.

6. The tool of claim 3, wherein the user control further includes a spring element mounted therein for normally biasing the slidable, rotatable dial to a longitudinal position wherein the tongs are forced together to grasp the lead.

7. The tool of claim 1, wherein the user control further includes a retainer rod extending within the shaft guide member and coupling the slidable, rotatable dial to the proximal end of the drive cable.

8. The tool of claim 1, wherein the stationary handle includes an inner annular extension received in a cavity formed at a proximal end of the slidable, rotatable dial.

9. The tool of claim 8 wherein:

the stationary handle includes a body and a pair of fingers extending distally from the body, the pair of fingers forming the aperture, the slidable, rotatable dial positioned between the pair of fingers and accessible for longitudinal and rotational manipulation via the aperture.

10. The tool of claim 8 wherein:

the slidable, rotatable dial having a first distal section and a second proximal section, the first distal section having a first diameter, the second proximal section having a second diameter smaller than the first diameter, the second proximal section receiving the inner annular extension, the first distal section comprising a plurality of grooves for facilitating user control.

11. The tool of claim 1, further comprising a retainer rod having a distal end and a proximal end, the retainer rod distal end held within a proximal end of the shaft guide member and the retainer rod proximal end held within a distal end of the stationary handle, the retainer rod distal end rotatable within the shaft guide member and the retainer rod proximal end rotatable within the stationary handle distal end, the retainer rod fixedly coupled to the slidable rotatable dial.

12. A epicardial lead implant tool comprising:

an elongate shaft including a proximal end and a distal end;

a gripping assembly terminating the distal end of the shaft and adapted to alternately grasp the epicardial lead and release the lead and to rotate the lead;

a drive cable coupled to the gripping assembly and extending proximally therefrom within the shaft; and a user control terminating the proximal end of the shaft and including a shaft guide member coupled to the shaft, the user control facilitates single-handed manipulation of the slidable, rotatable dial, a stationary handle coupled to the shaft guide member, a slidable, rotatable dial coupled to a proximal end of the drive cable and positioned in between the shaft guide member and the stationary handle, and an aperture formed between the shaft guide member and the handle to expose the slidable, rotatable dial.

* * * * *

UNITED STATES PATENT AND TRADEMARK OFFICE
CERTIFICATE OF CORRECTION

PATENT NO. : 7,637,916 B2 Page 1 of 1
APPLICATION NO. : 10/858228
DATED : December 29, 2009
INVENTOR(S) : Sandstrom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1290 days.

Signed and Sealed this

Ninth Day of November, 2010

David J. Kappos
*Director of the United States Patent and Trademark Office*